(12) United States Patent
Penza

(10) Patent No.: US 7,345,757 B2
(45) Date of Patent: Mar. 18, 2008

(54) INSPECTION APPARATUS FOR PIPELINES

(76) Inventor: G. Gregory Penza, 92 Central Pkwy., Huntington, NY (US) 11743

( * ) Notice: Subject to any disclaimer, the term of this patent is extended or adjusted under 35 U.S.C. 154(b) by 302 days.

(21) Appl. No.: 10/952,019

(22) Filed: Sep. 28, 2004

(65) Prior Publication Data

US 2006/0066847 A1    Mar. 30, 2006

(51) Int. Cl.
*G01N 21/00*   (2006.01)

(52) U.S. Cl. ................................. 356/241.1; 356/241.6

(58) Field of Classification Search ............... 356/428, 356/241.3; 348/82, 373; 396/376; 702/183
See application file for complete search history.

(56) References Cited

U.S. PATENT DOCUMENTS

| | | | |
|---|---|---|---|
| 4,063,283 A | 12/1977 | Rider et al. | |
| 4,302,772 A | 11/1981 | Gillot | |
| 4,331,975 A | 5/1982 | Krawza et al. | |
| 4,704,897 A | 11/1987 | Kawase et al. | |
| 5,045,936 A | 9/1991 | Lobb et al. | |
| 5,425,279 A | 6/1995 | Clark et al. | |
| 5,604,532 A | 2/1997 | Tillmanns | |
| 5,611,283 A | 3/1997 | Cotton et al. | |
| 5,612,499 A | 3/1997 | Andrew et al. | |
| 5,654,795 A | 8/1997 | Dierlam | |
| 5,717,455 A | 2/1998 | Kamewada | |
| 5,754,220 A | 5/1998 | Smalser, Sr. | |
| 5,956,077 A * | 9/1999 | Qureshi et al. ............... 348/82 |
| 6,028,719 A | 2/2000 | Beckstead et al. | |
| 6,111,600 A | 8/2000 | McLeod et al. | |
| 6,259,523 B1 | 7/2001 | Welker | |
| 6,313,869 B1 | 11/2001 | Hyp et al. | |
| 6,338,359 B1 | 1/2002 | Welker | |
| 6,359,645 B1 | 3/2002 | Sivacoe | |
| 6,392,692 B1 | 5/2002 | Monroe | |
| 6,437,853 B2 | 8/2002 | Seo | |
| 6,538,732 B1 | 3/2003 | Drost et al. | |
| 6,545,704 B1 | 4/2003 | Olsson et al. | |
| 2002/0003584 A1 * | 1/2002 | Kossin ....................... 348/373 |
| 2002/0190682 A1 | 12/2002 | Schempf et al. | |

OTHER PUBLICATIONS

Aries Industries, Inc., "GasCam Video Inspection System," [retrieved on May 22, 2002]. Retrieved from URL: http://www.ariesind.com/gascam.html.

* cited by examiner

*Primary Examiner*—Tarifur Chowdhury
*Assistant Examiner*—Tara S Pajoohi
(74) *Attorney, Agent, or Firm*—Brooks Kushman P.C.

(57) ABSTRACT

An inspection system is provided that includes a camera and a laser distance measuring device. The camera has high magnification capabilities and can be panned and tilted as needed. The laser distance measuring device provides information regarding the distance from the camera to the object being imaged. The camera and laser distance measuring device are carried by a frame, which has an elongated member attached thereto for resting the frame on a surface. This configuration makes the inspection system well suited to inspect horizontal pipelines without feeding the camera along the length of the pipeline.

23 Claims, 7 Drawing Sheets

INSPECTION APPARATUS FOR PIPELINES

BACKGROUND OF THE INVENTION

1. Field of the Invention

The present invention relates to an inspection apparatus, and more particularly, to an inspection apparatus suitable for inspecting long pipelines.

2. Background Art

For more than 30 years, video inspection has been a baseline fundamental analytical tool for the evaluation and assessment of pipeline integrity. Originally developed as an aid for sewer system maintenance, video inspection equipment and techniques have played a key role in the development of "no-dig" and "trenchless" pipeline rehabilitation methods. This is because the choice of the best trenchless rehabilitation method, for any given application, is often largely based on the video inspection that takes place prior to the rehabilitation. Thus, the information gleaned from the pre-rehabilitation video inspection is used as the basis for key decisions that drive the entire rehabilitation process.

The inspection of pipes often falls into two broad categories: inspections performed for purposes of preventative maintenance, and inspections performed as a response to a need for repair maintenance. The former category may include such things as locating cracks in the pipeline prior to their reaching a critical length, discovering the location of unknown branches or service tees, determining the exact location of valves and fittings, and finding water within the pipeline. In general, video inspection equipment is useful as a proactive tool for assessing the cleanliness, corrosion, and structural integrity of the pipeline. In the case of repair maintenance, high quality video inspection data is also very important.

Over the years, a myriad of inspection devices have been developed for use inside pipelines. Many of these require a device to carry a camera down the length of the pipeline to capture images that are distant from a manhole, or other pipeline entrance. Other devices rely on a camera having zoom capabilities to capture images at some distance from the pipeline entrance. One such device is described in U.S. Pat. No. 6,538,732, issued to Drost et al. on Mar. 25, 2003. The inspection system described in Drost et al. includes a camera having magnification functionality, one or more lights used to illuminate an object to be imaged, and a power supply and controller for controlling operation of the camera. In addition, the inspection system described in Drost et al. may include a measuring system that can be used to determine the size of an object being imaged.

One limitation of the inspection system described in Drost et al. is that it lacks a mechanism for determining how far the imaged object is from the camera. Thus, an operator will not know where in the pipeline the imaged object can be found. Because a camera may be imaging a portion of the pipeline that needs cleaning or repair, information regarding the specific location of imaged objects is important, and may save both time and money. Another limitation of the inspection system described in Drost et al. is that it needs to be held by an operator to position the camera to capture images of the pipeline. Indeed, even after the camera begins collecting images, the operator is still required to support the device while it is in use. Such a system may lead to operator fatigue, or may result in a reduction in image quality if the operator is unable to hold the camera still while it is capturing images.

Another inspection device is described in U.S. Pat. No. 4,331,975, issued to Krawza et al. on May 25, 1982. Krawza et al. describes instrumentation for surveying underground cavities. The instrumentation includes a television camera and two light sources mounted on a frame which is vertically supported by a cable. The frame assembly is lowered into a bore hole via the cable by a power-driven winch. After being lowered into the bore hole, the frame is supported on the ground by four rubber-capped feet. The instrumentation is configured to provide information about underground cavities, such as mines and caves. For example, cameras attached to the frame can take video or still photographs of the cavity. In addition, the two light sources can be manipulated to provide some information regarding the distance of a cavity wall from the frame. In particular, one of the light sources can be tilted, and if both light sources are focused on the same point, the distance from the frame to that point can be calculated using trigonometry.

One limitation of the instrumentation described in Krawza et al. is that it may not be suitable to inspect pipelines. For example, the video camera is rigidly fixed to the frame, and although the instrumentation may include a pan and tilt mechanism, the camera remains at a fixed distance from the ground. This may not be suitable for inspecting horizontal pipelines, which have a variety of different diameters. Another limitation of the instrumentation described in Krawza et al. is that the position of the frame is not easily manipulated because it is suspended from a cable, rather than having a rigid member attached to it, which would more readily facilitate positioning of the frame. In addition, the system of distance measuring, which relies on two separate lights to focus on the same object, is undesirably complicated, and for horizontal pipeline inspections, it may be unworkable.

Therefore, a need exists for an inspection apparatus capable of providing image and distance information for objects in a pipeline, and capable of being easily positioned, thereby facilitating inspection.

SUMMARY OF THE INVENTION

Accordingly, the present invention provides an inspection system including an imaging device configured to output a signal related to an object being imaged. The inspection system also includes a distance measuring device configured to determine a distance between the imaging device and an object to be imaged, and to output a signal related to the determined distance. A light source is configured to direct light on the object to be imaged, and a frame carries the imaging device, the distance measuring device, and the light source. A first elongated member defines a first axis, and has one end attached to the frame. The first elongated member is generally rigid, thereby facilitating positioning of the imaging device. A second elongated member defines a second axis, and has a first end attached to the frame. The second elongated member also has a second end configured to rest on a surface, thereby supporting the frame at some distance from the surface.

The invention also provides an inspection system including an imaging device configured to output a signal related to an object being imaged. A distance measuring device is configured to determine a distance between the imaging device and an object to be imaged, and configured to output a signal related to the determined distance. A light source is configured to direct light on the object to be imaged. The imaging device, the distance measuring device, and the light source are attached to a frame. The frame includes first and second side members, and first and second beams disposed between the first and second side members. The first and second beams are substantially parallel to each other. The first beam includes an attachment feature for facilitating attachment of the frame to a support structure. A first motor is attached to the first beam, and is configured to cooperate with the attachment feature for rotating the frame about a first axis. A second motor is disposed within the first beam and attached to the first side member. The second motor is operable to rotate the imaging device, the distance measuring device, and the light source about an axis generally perpendicular to the first axis.

DETAILED DESCRIPTION OF THE PREFERRED EMBODIMENT(S)

Figure 1:
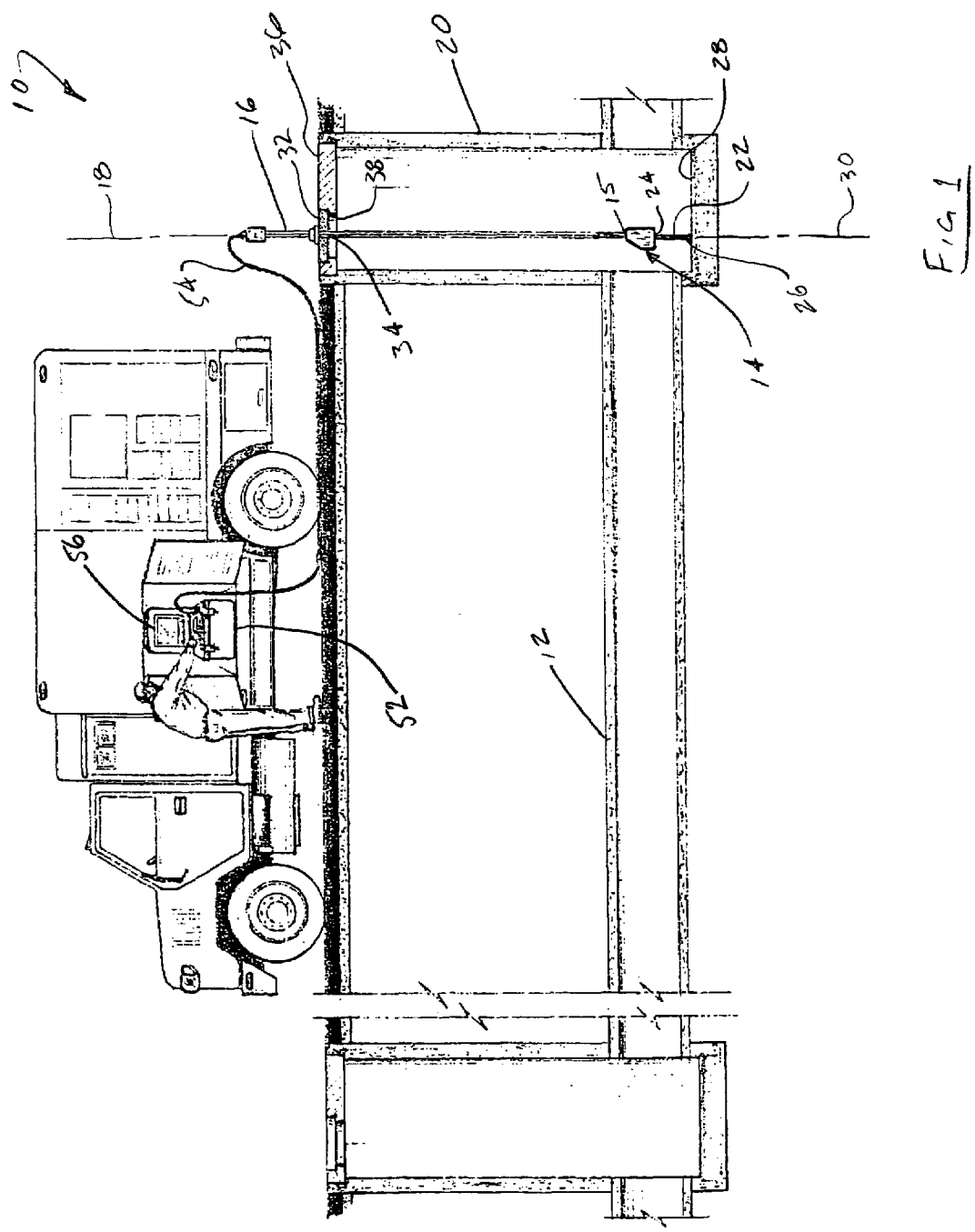
FIG. 1 shows an inspection system in accordance with the present invention, the inspection system being used to inspect a horizontal sewer pipe.
Figure 2:
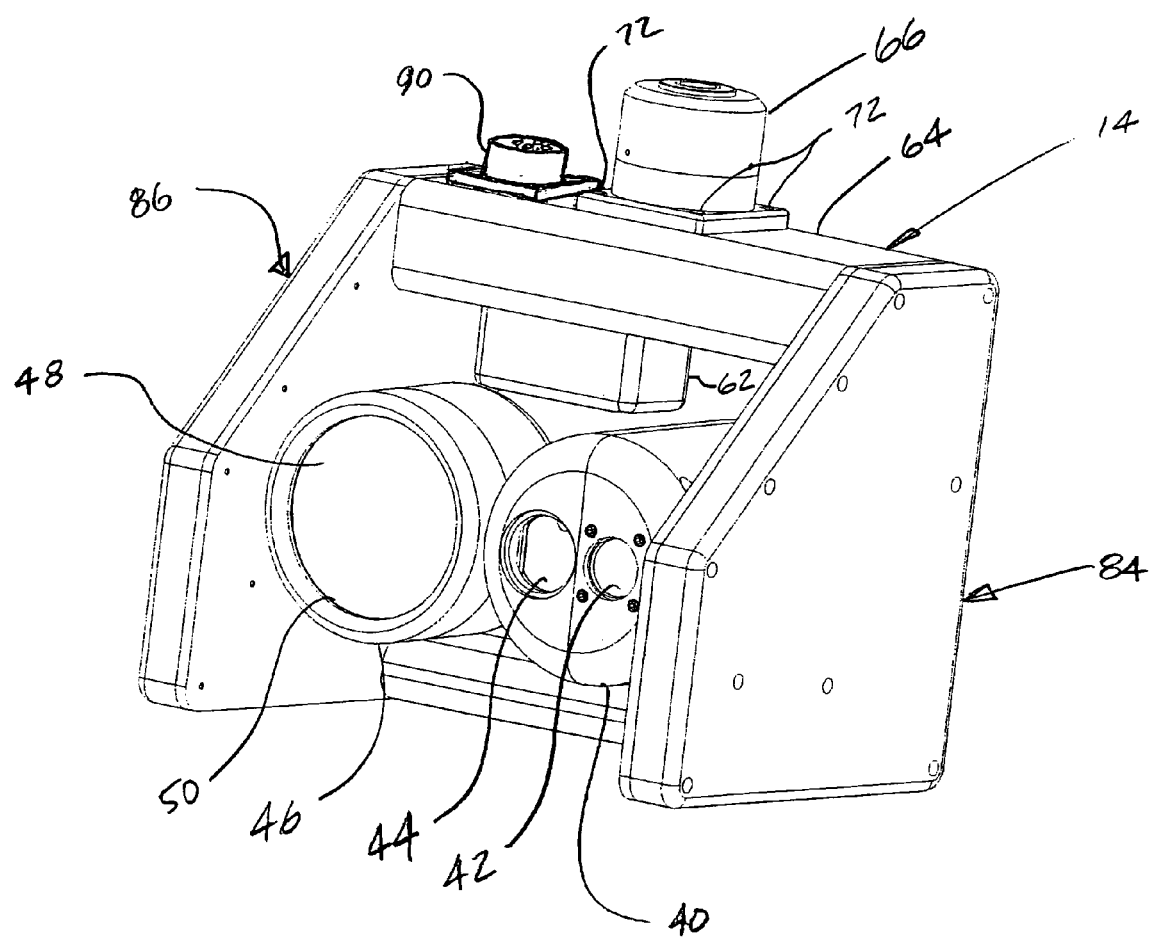
FIG. 2 is a perspective view of a portion of the imaging system, including a frame having two water resistant housings attached thereto.

FIG. 1 shows an inspection system 10 in accordance with the present invention. Although the inspection system 10 may be used to capture image and distance data in a wide variety of applications, it is illustrated and described herein as used in inspection of a horizontal sewer pipe 12. The inspection system includes a frame 14, which, as shown in FIG. 2, carries a number of different components, each of which is explained in more detail below. Returning to FIG. 1, the frame 14 is attached to one end 15 of a first elongated member, or guide pole 16. The guide pole 16 is generally rigid, thereby facilitating easy manipulation and positioning of the frame 14, especially as compared to suspending the frame 14 from a cable. The guide pole 16 defines a first axis 18 which, as shown in FIG. 1, is generally parallel to a manhole 20 and perpendicular to the sewer pipe 12. A second elongated member, or rest 22, has one end 24 attached to the frame 14, and a second end 26 configured to rest on a surface, such as the floor 28 of the manhole 20. The rest 22 supports the frame 14 some distance from the floor 28 so that image and distance data can be gathered from inside the sewer pipe 12. Although it is shown resting on the floor 28 of the manhole 20, the second end 26 of the rest 22 may be conveniently placed on an invert or shelf within a manhole, or on other surfaces, depending on the area being inspected. The rest 22 defines a second axis 30, which, in a configuration shown in FIG. 1, is coincident with the first axis 18.

Although the guide pole 16 is shown in FIG. 1 as a single piece, it may conveniently be formed from a number of pieces which slide into and out of each other, thereby providing a telescoping feature which is convenient to accommodate different depths, and is also convenient for storage and transport. To provide lateral support for the guide pole 16, a flange 32 is provided. The flange includes an aperture 34 through which the guide pole 16 can be placed. The flange 32 is configured to cooperate with a manhole casting 36. One convenient configuration involves forming the flange 32 from a piece of steel or aluminum flat stock that is bent into a radius to rest on a lip 38 of the manhole casting 36. Of course, flanges, such as the flange 32, can be made from a variety of different materials, and made into a variety of different configurations to perform the basic function of providing lateral support to the guide pole 16.

Figure 3:
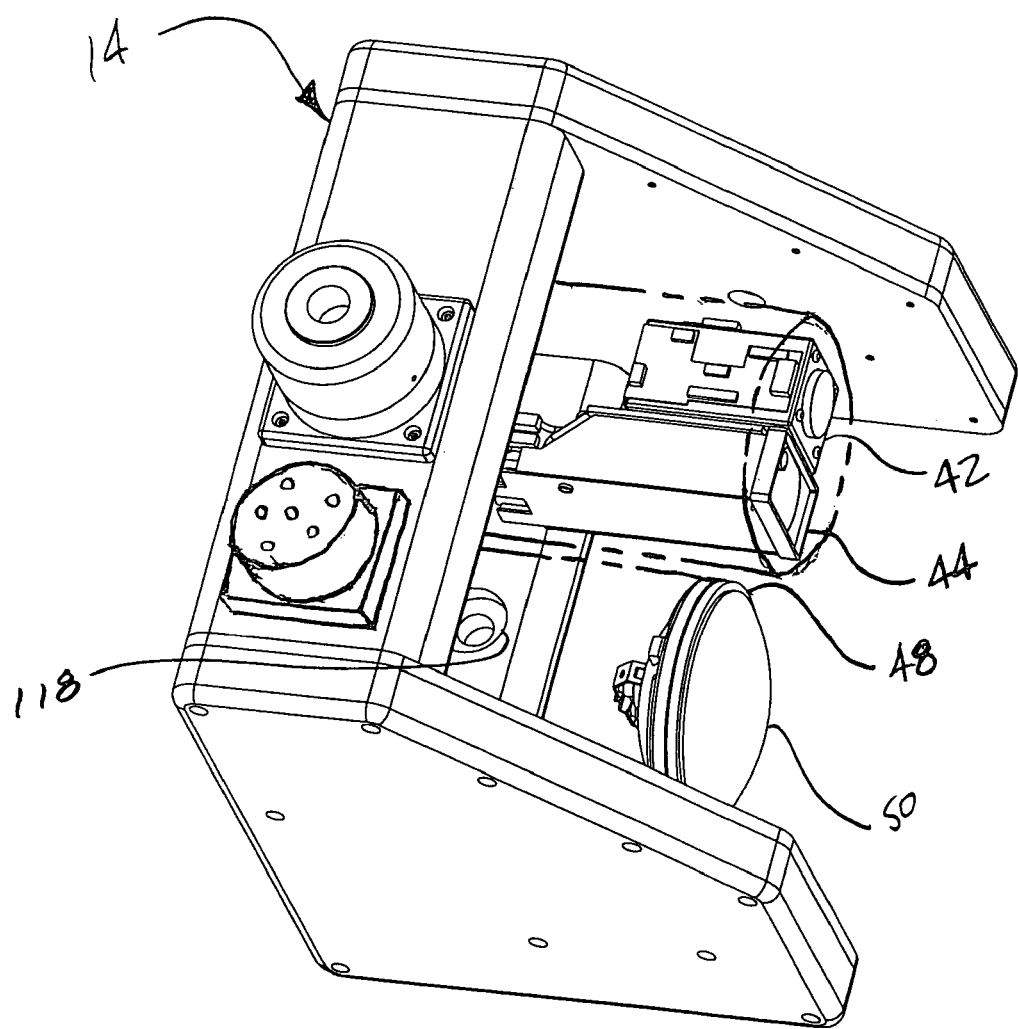
FIG. 3 is a perspective view of the frame showing the housings in phantom to reveal a camera, a laser distance measuring device, and a light.

FIG. 2 shows the frame 14 and various components of the inspection system attached to it. For example, a first housing 40 contains an imaging device, such as a camera 42, and a distance measuring device, such as a laser distance measuring device 44. Although a laser distance measuring device is shown in this embodiment, other distance measuring devices, such as those utilizing other types of lights or sound may be used. A second housing 46 contains a high-intensity light 48 that is used to illuminate objects being imaged in the sewer pipe 12. FIG. 3 shows the frame 14 with the housings 40, 46 in phantom to reveal the camera 42, the laser distance measuring device 44, and the light 48. In order to capture image data for distant objects, the camera 42 is equipped with a combination optical and digital zoom capability. The high-powered optical zoom of the camera 42 provides a 25:1 magnification. In addition, the camera 42 includes a 12:1 digital zoom, thereby providing a 300:1 zoom capability. This allows objects more than 100 feet from the camera 42 to be clearly imaged. This is particularly important in pipeline inspection applications, where access points may be hundreds of feet apart. Hence, the inspection system 10 does not require the camera 42 to be fed down the length of a sewer pipe, such as the sewer pipe 12, but rather, the camera 42 can conveniently remain in a manhole during the inspection process.

In order to illuminate distant objects, the light 48 is provided with a collimating lense 50, shown in FIGS. 2 and 3. Providing the light 48 with the collimating lense 50 produces a straight beam of light which can illuminate distant objects even in a sewer pipe. In the event that images outside the reach of the light 48 are desired, the camera 42 can be configured for image enhancement. For example, the camera 42 can be configured with active or passive infrared technology to capture images of objects that are not clearly illuminated by the light 48 or some other light source.

A distance measuring device, such as the laser distance measuring device 44, can be purchased as a separate component and integrated into the imaging system 10, or alternatively, it can be custom-designed and built specifically for a particular application. The camera 42 and the light 48 can also be purchased separately and integrated into the imagining system 10, or they may be custom designed and built. The laser distance measuring device 44 is mounted in close proximity to the camera 42. In this way, an object being imaged will be essentially the same distance from the camera 42 and from the laser distance measuring device 44. Therefore, the distance measured by the laser distance measuring device 44 can be assumed to be the distance between the camera 42 and the object being imaged.

Each of the three components—the camera 42, the laser distance measuring device 44, and the light 48—are connected to a controller 52 by a cable 54—see FIG. 1. In addition to controlling the operation of the camera 42, the laser distance measuring device 44, and the light 48, the controller 52 is also configured to receive signals related to image and distance data from the camera 42 and the laser distance measuring device 44. The controller 52 can then effect storage of the information on a device, such as a computer hard drive or other storage medium. In addition, the controller 52 can provide information to an output device, such as a monitor 56 (see FIG. 1), so that a technician can monitor an inspection in real time. Information from the camera 42 and the laser distance measuring device 44 can be integrated by the controller 52, such that a distance measurement is displayed along with a captured image, so that a technician can remotely observe an object, and at the same time, know the location of the object.

Figure 4:
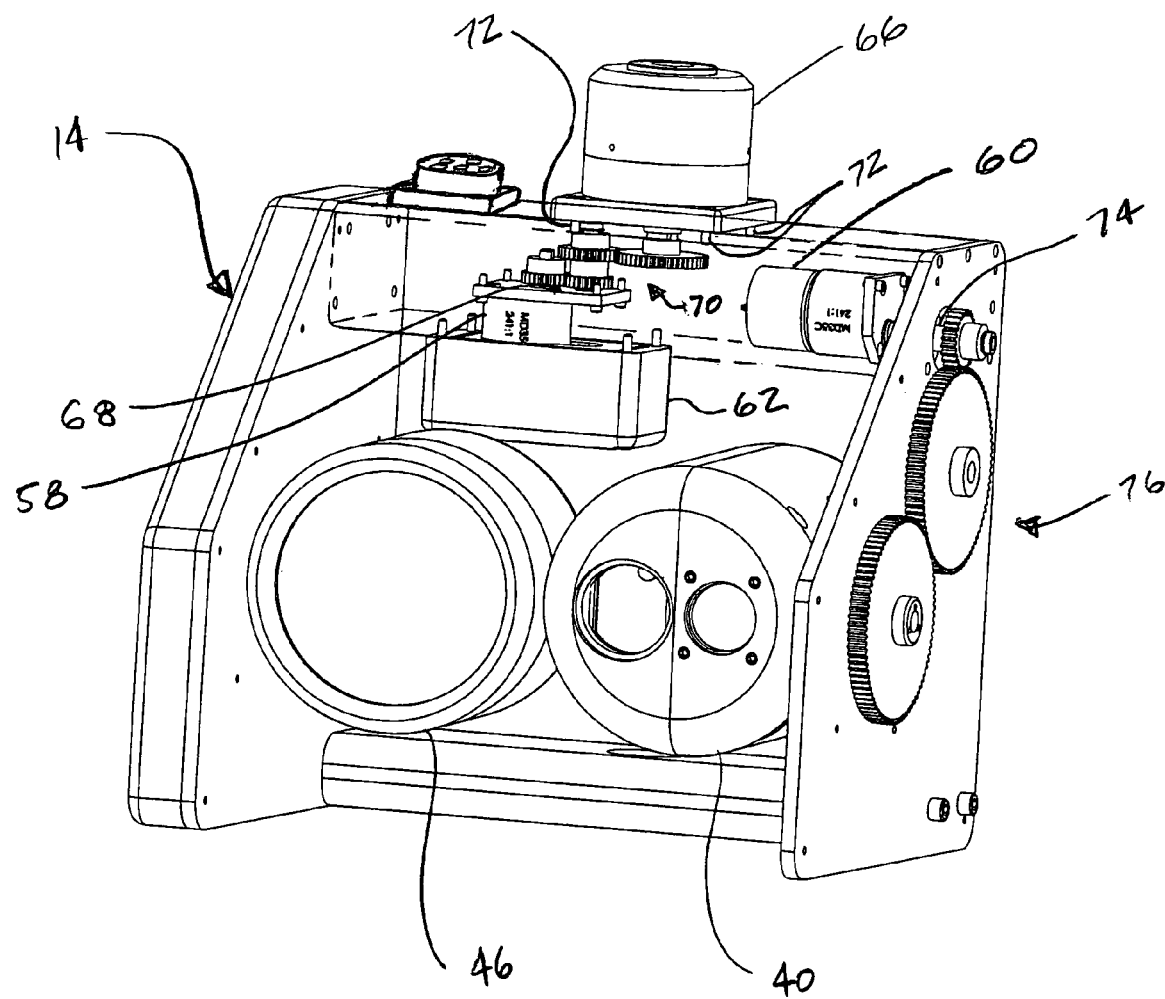
FIG. 4 is a perspective view of the frame showing the upper beam in phantom to reveal a pair of motors and gearsets used to pan and tilt the frame and housings to desired orientations.

In addition to controlling the operation of the camera 42, the laser distance measuring device 44, and the light 48, the controller 52 also controls the operation of two motors 58, 60—see FIG. 4. In FIG. 4, a portion of the frame 14 is shown in phantom to reveal the motors 58, 60. The first motor 58 resides in a motor housing 62 which is attached to a first, or upper beam 64—see FIG. 2. Also disposed on the upper beam 64 is an attachment feature, or hub 66—see FIG. 2. FIG. 4 shows how an output shaft 68 of the first motor 58 cooperates with the hub 66 through a number of gears 70. The hub 66 is configured to facilitate attachment of a support structure, such as the guide pole 16. Alternatively, the entire frame 14 can be attached to other types of support structures, for example, a tripod—in which case, the frame 14 is rotated 180° from its orientation shown in FIG. 1.

To effect a secure attachment between a support structure, such as the guide pole 16, and the hub 66, a transverse pin (not shown) may be inserted through apertures (not shown) in the guide pole 16 and the hub 66. Of course, other types of attachments can be used as desired. The hub 66 is secured to the upper beam 64 with four fasteners 72, only three of which are visible in FIGS. 2—4. Therefore, with a support structure, such as the guide pole 16 securely attached to the hub 66, and the hub 66 securely attached to the upper beam 64, rotation of the output shaft 68 effects a rotation of the frame 14 about the first axis 18.

Figure 5:
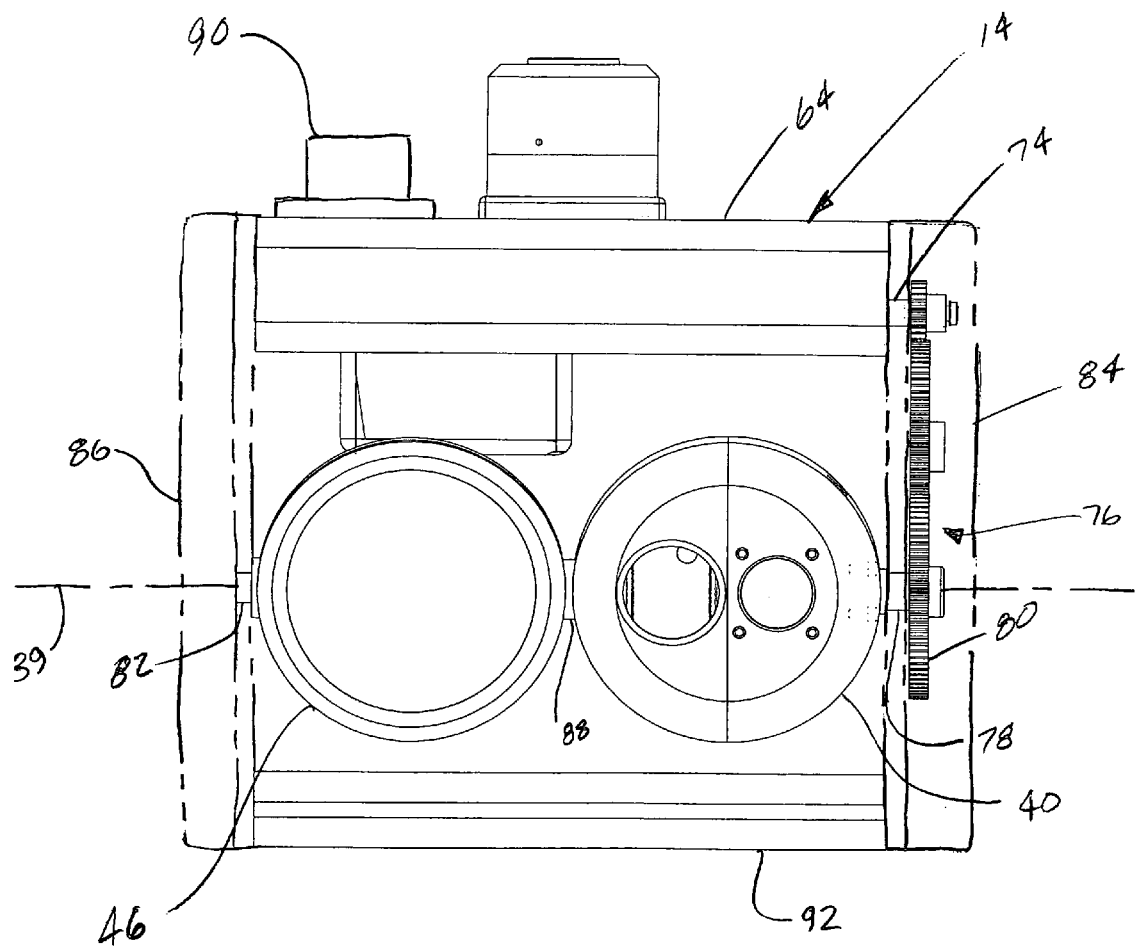
FIG. 5 is a front view of the frame illustrating how the housings are tilted.

The second motor 60 can also be controlled by the controller 52 to position the camera 42, the laser distance measuring device 44, and the light 48. The second motor 60, in the embodiment shown in FIGS. 2-4, is completely disposed within the upper beam 64. As shown in FIG. 4, the second motor 60 includes an output shaft 74 that cooperates with a plurality of power transmission elements, or gears 76, to transfer rotational motion from the output shaft 74 to the housings 40, 46. FIG. 5 shows how the output shaft 74 transfers rotational motion through the gears 76 to the first housing 40. Attached to the first housing 40 is a trunnion 78 which is attached to a spur gear 80 of the gears 76. Also shown in FIG. 5 is a second trunnion 82 attached to the second housing 46. Each of the trunnions 78, 82 are supported on side members 84, 86, shown in phantom in FIG. 5, and together the trunnions 78, 82 define an axis 89 that is generally perpendicular to the first axis 18. Because the housings 40, 46 are connected together by a link 88, they pivot together about the axis 89, thereby aiming the camera 42, the laser distance measuring device 44, and the light 48 at the same object. In order to provide electrical communication between the controller 52 and the various devices carried by the frame 14, an electrical connector 90 is provided. The connector 90 is configured for fast attachment to and from a cable, such as the cable 54, and is also configured to provide a watertight seal if an appropriate cable connector is used.

In addition to the upper beam 64, and the two side members 84, 86, the frame 14 also includes a second, or lower beam 92. The lower beam 92 is substantially parallel to the upper beam 64, and like the upper beam 64 is disposed between the first and second side members 84, 86. Although the lower beam 92 is, in the configuration shown in FIGS. 1-5, a solid structural member, it may be configured like the upper beam 64, or the side member 84, to house additional components. In fact, the upper beam and the side member 84 provide water resistant housings for the second motor 60 and the gears 76, respectively. Because the inspection system 10 may be used in wet or dirty environments, the frame 14 provides a water resistant enclosure for each of the elements disposed therein. Similarly, the first and second housings 40, 46 are also water resistant, and in fact, are waterproof to a submerged depth of 100 feet. The frame 14 and the housings 40, 46 are made from anodized aluminum having rubber seals disposed between individual pieces. The use of impact-resistant polymers for the frame 14 and housings 40, 46 is also contemplated.

Figures 6, 7:
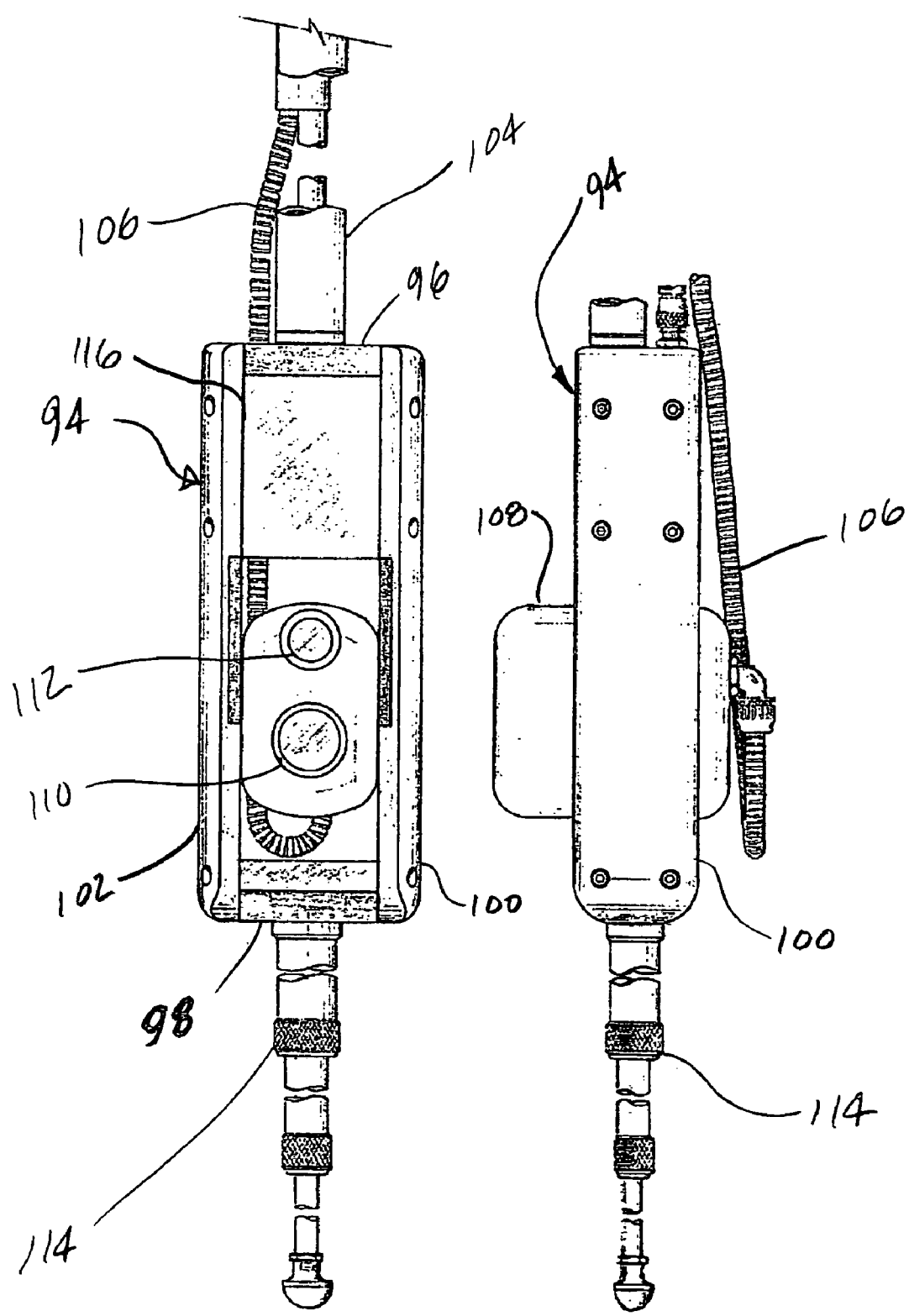
FIG. 6 is a front view of an alternative embodiment of the frame carrying a single water resistant housing.
FIG. 7 is a side view of the frame shown in FIG. 6.

As shown in FIG. 5, the frame 14 has a generally square shape when viewed from the front. Of course, other configurations can be used, for example, when access to an object to be imaged is through a very small opening. FIGS. 6 and 7 show one such configuration. A frame 94 is configured with a narrow profile that facilitates entry through very small openings. As with the frame 14, the frame 94 includes upper and lower beams 96, 98 that are disposed between two side members 100, 102. Attached to the upper beam 96 is a guide pole 104 which may be similarly configured to the guide pole 16, shown in FIG. 1. A cable 106 is provided to facilitate electrical communication between a controller, such as the controller 52 shown in FIG. 1, and the electrical components attached to the frame 94. Attached to the frame 94 is a single water resistant housing 108. The housing 108 seals and protects a camera and a laser distance measuring device which are disposed behind a first lens 110. The housing 108 also seals and protects a light, which is disposed behind a second lens 112. Similar to the embodiment shown in FIG. 1, the frame 94 has a rest 114 attached to the lower beam 98. The rest 114, like the rest 22, includes a number of telescoping sections which can be expanded or contracted to change the resting height of the frame 94. The frame 94 also includes an upper compartment 116 which can be used to house one or more motors to articulate the frame 94 and the housing 108 to a desired position.

Figure 8:
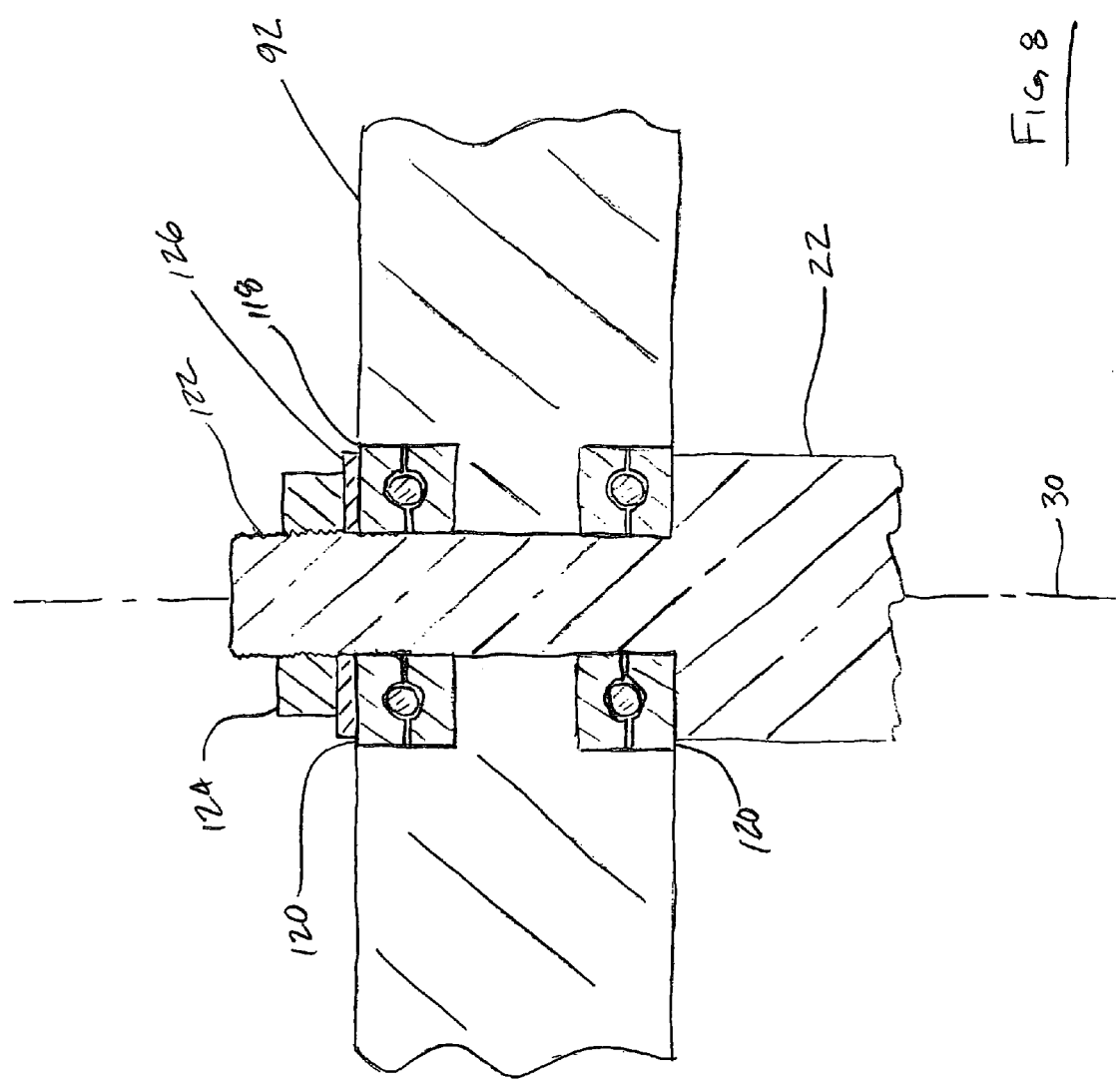
FIG. 8 is a fragmentary sectional view of a portion of a rest used to support the frame at some distance from a surface.

The connection of the rest 114 to the frame 94 may be the same as connection of the rest 22 to the frame 14, which is illustrated in FIG. 8. The lower beam 92 of the frame 14 includes an aperture 118 that is counterbored on both sides of the lower beam 92—see also FIG. 3. Each of the counterbores acts as a bearing seat for a thrust bearing 120. The rest 22 includes a shaft 122, an upper portion of which is threaded. The shaft 122 can be inserted through the aperture 118, through the bearings 120, and secured with a nut 124, and optionally, a washer 126. With this configuration, the second end 26 of the rest 22 can remain stationary on a surface, such as the manhole floor 28 while the frame 14 is rotated by the first motor 58. Thus, the inspection system 10 provides both pan and tilt capabilities to capture images of objects at virtually any angle from the camera 42.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An inspection system, comprising:
   an imaging device configured to output a signal related to an object being imaged;
   a light source configured to direct light on the object to be imaged;
   a frame for carrying the imaging device and the light source;

a first elongated member defining a first axis and having an end configured for insertion through an opening proximate an area to be inspected, the end being attached to the frame such that the frame is carried on the first elongated member and the frame is inserted through the opening when the end is inserted through the opening to position the frame proximate the area to be inspected, the first elongated member being generally rigid, thereby facilitating positioning of the imaging device carried by the frame; and a second elongated member defining a second axis and having a first portion attached to the frame such that the second elongated member is carried on the frame and the second elongated member is inserted through the opening when the frame is inserted through the opening to position the second elongated member proximate the area to be inspected, the second elongated member further having a second portion configured to rest on a surface accessible through the opening, thereby supporting the frame at some distance from the surface.

2. The inspection system of claim 1, wherein the second elongated member includes a bearing for facilitating rotation of the frame about the second axis while the second end of the second elongated member remains stationary.

3. The inspection system of claim 1, wherein the first axis is substantially coincident with the second axis.

4. The inspection system of claim 1, further comprising a first motor attached to the frame and configured to cooperate with a portion of the frame for rotating the frame about the first axis.

5. The inspection system of claim 4, further comprising at least one water resistant housing, the at least one water resistant housing being configured to house the imaging device and the light source.

6. The inspection system of claim 5, further comprising a second motor attached to the frame and configured to cooperate with the at least one housing for pivoting the at least one housing about an axis generally perpendicular to the first axis.

7. The inspection system of claim 1, further comprising at least one controller configured to control operation of the imaging device and the light source, the at least one controller being further configured to receive signals output from the imaging device and the distance measuring device.

8. The inspection system of claim 1, further comprising a distance measuring device configured to determine a distance between the imaging device and the object to be imaged, and to output a signal related to the determined distance.

9. The inspection system of claim 1, further comprising a flange having an aperture for receiving the first elongated member therethrough, the flange being configured to cooperate with a manhole casting, thereby providing lateral support for the first elongated member when the imaging device is placed within a manhole.

10. The inspection system of claim 1, wherein the imaging device includes an infrared light source, and the imaging device is configured to capture infrared images.

11. The inspection system of claim 1, wherein the light source includes a collimating lens for focusing the light emitted from the light source.

12. The inspection system of claim 1, wherein the imaging device includes zoom capabilities of at least 100:1.

13. An inspection system, comprising:
an imaging device configured to output a signal related to an object being imaged;

a distance measuring device configured to determine a distance between the imaging device and an object to be imaged, and to output a signal related to the determined distance;

a light source configured to direct light on the object to be imaged;

a frame having the imaging device, the distance measuring device, and the light source attached thereto, the frame including first and second side members, and first and second beams disposed between the first and second side members and substantially parallel to each other, the first beam including an attachment feature for facilitating attachment of the frame to a support structure;

a first motor attached to the first beam, and configured to cooperate with the attachment feature for rotating the frame about a first axis; and a second motor disposed within the first beam and attached to the first side member, the second motor being operable to rotate the imaging device, the distance measuring device, and the light source about an axis generally perpendicular to the first axis.

14. The inspection system of claim 13, further comprising a first elongated member attached to the attachment feature and disposed along the first axis for positioning the imaging device.

15. The inspection system of claim 14, further comprising a second elongated member having a first end attached to the second beam, and a second end configured to rest on a surface, thereby supporting the frame at some distance from the surface.

16. The inspection system of claim 13, wherein the first side member includes at least one power transmission element disposed therein, the at least one power transmission element being configured to transfer rotational motion from the second motor to the imaging device, the distance measuring device, and the light source.

17. The inspection system of claim 13, further comprising at least one water resistant housing, the at least one water resistant housing being configured to house the imaging device, the distance measuring device, and the light source.

18. The inspection system of claim 13, further comprising at least one controller configured to control operation of the imaging device, the distance measuring device, and the light source, the at least one controller being further configured to receive signals output from the imaging device and the distance measuring device.

19. The inspection system of claim 13, wherein the distance measuring device includes a laser distance measuring device.

20. The inspection system of claim 13, further comprising a flange having an aperture for receiving the first elongated member therethrough, the flange being configured to cooperate with a manhole casting, thereby providing lateral support for the first elongated member when the imaging device is placed within a manhole.

21. The inspection system of claim 13, wherein the imaging device includes an infrared light source, and the imaging device is configured to capture infrared images.

22. The inspection system of claim 13, wherein the light source includes a collimating lens for focusing the light emitted from the light source.

23. The inspection system of claim 13, wherein the imaging device includes zoom capabilities of at least 100:1.

* * * * *